United States Patent [19]

Friedman

[11] 4,079,515

[45] Mar. 21, 1978

[54] IMPLANT DEVICES FOR RETAINING DENTURES

[75] Inventor: Joel Friedman, New York, N.Y.

[73] Assignee: Bentley Laboratories, Inc., Irvine, Calif.

[21] Appl. No.: 633,232

[22] Filed: Nov. 19, 1975

[51] Int. Cl.² .................................... A61C 13/00
[52] U.S. Cl. .................................... 32/10 A
[58] Field of Search .................... 32/10 A

[56] References Cited

U.S. PATENT DOCUMENTS

| 3,465,441 | 9/1969 | Linkow | 32/10 A |
| 3,579,829 | 5/1971 | Sampson | 32/10 A |
| 3,628,248 | 12/1971 | Kroder | 32/10 A |
| 3,797,113 | 3/1974 | Brainin | 32/10 A |

FOREIGN PATENT DOCUMENTS

| 2,154,272 | 5/1973 | Germany | 32/10 A |
| 540,713 | 3/1956 | Italy | 32/10 A |

Primary Examiner—Robert Peshock
Attorney, Agent, or Firm—Lyon & Lyon

[57] ABSTRACT

An implant device for retaining dentures comprised of a barrel portion capable of receiving a denture retaining means, preferably a magnet, and a base portion integrally formed with the barrel portion. The base portion is provided with a flange having a plurality of apertures formed therein. The device is capable of being permanently implanted into the mouth of a patient.

4 Claims, 2 Drawing Figures

IMPLANT DEVICES FOR RETAINING DENTURES

BACKGROUND OF THE INVENTION

The present invention relates to implant devices and, in particular, relates to implant devices for retaining dentures.

Unsatisfactory dentures have presented a continual problem to the patient and dentist. In the past, dentures were retained in place in the mouth on the edentulous ridges by two forces, a peripheral seal which produced a partial vacuum and an interfacial surface tension which involved an intimate fit of tissue to the surface of the denture aided by a film of saliva. With aging and disease of the alveolar bones of the maxilla and mandible, the edentulous ridges progressively atrophied. With atrophication and reabsorption of bony tissues of the edentulous ridges, the ridges were incapable of effectively retaining dentures. The dentures were easily dislodged with mastication, speech and all other oral functions. Recurrent soreness of the mouth tissues ensued and adjusting the remaking the dentures did not solve the problem.

Several prior methods have been utilized to aid denture retention. Firstly, denture adhesives have been utilized. Unfortunately, denture adhesives rapidly deteriorate thereby losing their effectiveness and becoming unhygienic. Secondly, full subperiosteal implant devices have also been used to retain dentures. The arch-shaped device consisted of a metal such as vitallium and was implanted into the mouth below the periosteum. The device was secured by screws and was provided with four abutment posts which protruded through the mucosa to serve as a point of attachment for the dentures. The dentures were provided with retaining clasps which were clipped onto the abutment posts. Unfortunately, the procedure for implanting the device required two radical surgical procedures and therefore was not suitable for many patients. Lastly, intra-boney implant devices have been utilized to retain dentures. The metallic devices were inserted into the alveolar bone and functioned as abutments for the dentures. The devices were fabricated in the form of blades which were tapped into place in a trench cut in the alveolar bone, screws which were secured into the alveolar bone with a ratchet wrench and a tripod of pins which were inserted into the alveolar bone. Unfortunately, in many cases, the foreign body reaction of the bone to the metallic implant resulted in pain, bone destruction, infection and rejection of the implant thereby necessitating the subsequent removal of the implant.

SUMMARY OF THE INVENTION

It is, therefore, an object of the present invention to provide an implant device capable of retaining dentures.

This and other objects and advantages are obtained by forming an implant device for retaining dentures comprised of a barrel portion integrally formed with a base portion. The barrel portion performs or is provided with means for performing a denture retaining function, e.g., by inserting retaining means into a cavity in the barrel. It is preferred that the retaining means be a magnet which is installed into a cavity in the barrel prior to implantation, e.g., with the use of epoxy or dental cement. The base portion is preferably saddle-shaped and preferably has a plurality of apertures formed therein. The implant is preferably comprised of a material which is non-porous, biocompatible and non-biodegradable. The device is capable of being permanently implanted into the mouth of the patient. To implant the device, the edentulous mucosa is preferably retracted to expose the underlying maxillary or mandibulary ridge. The ridge may be altered by means of a bone bur to promote adequate and stable contact between the ridge and implant. The base of the device is positioned over the ridge of the mucosa is folded back over the outer surface of the device leaving the distal portion of the barrel protruding through the mucosa. A magnet having opposite polarity is permanently positioned on the surface of the denture so that when the denture is placed in the mouth, the magnets are contiguous.

BRIEF DESCRIPTION OF DRAWINGS

A more thorough disclosure of the objects and advantages of the present invention is presented in the detailed description which follows and from the accompanying drawings of which.

DETAILED DESCRIPTION OF INVENTION

Figure 1:
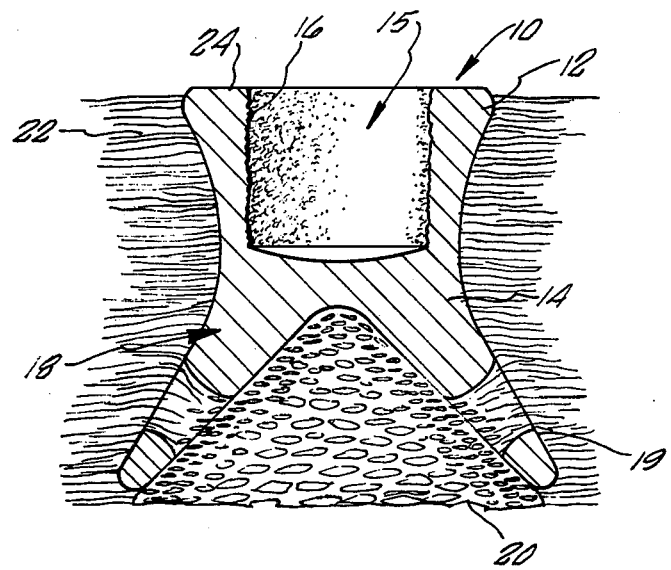
FIG. 1 is a sectional view taken along line 1—1 of FIG. 2 of the denture retaining device implanted into the mouth of the patient.

The present invention contemplates the formation of an implant device for retaining dentures. In the preferred embodiment, the implant is comprised of a barrel portion integrally formed with a base portion. The barrel portion preferably defines a cavity which functions to receive a suitably shaped means capable of retaining the dentures. The surface of the cavity is preferably serrated or roughened to facilitate attachment of a retaining means. The retaining means is preferably installed into the device with the use of epoxy or dental cement before the device is implanted into the mouth of the patient. Although it is preferred that the retaining means be a magnet, such as a cobalt magnet, it will be obvious to one skilled in the art that other suitable retaining means may also be used such as springs, clips, snap-locks, etc.. The base portion of the device is provided with a flange which is preferably saddle-shaped. The flange functions to receive the maxillary or mandibulary ridge is preferably provided with a plurality of apertures. The flange may be formed in other shapes or may be flat for implantation of the device into other areas of the mouth. The apertures are preferably round or ellipsoid but may also be slots or irregularly shaped holes. The apertures function to facilitate permanent attachment of the implant to the ridge and/or surrounding tissues in the mouth of the patient.

The implant device is comprised of a material which is preferably non-porous, biocompatible and non-biodegradable. The implant device is thus capable of being positioned in a permanent fashion mostly below the surface of the mucous membrane without causing tissue reaction infections or rejection by the body.

It is preferred that the material be essentially non-porous to permit the discharge of waste products along the surface of the device. The presence of pores will enable the accumulation of these waste products in the pores which will result in the subsequent necrosis of adjacent tissue. The implant device is preferably formed of carbon derived from polymer such as a highly polished vitreous (glassy) carbon or a pyrolytic carbon disposed onto a substrate such as graphite. The carbon is substantially pure, e.g. 98% pure, and is effectively non-porous, biocompatible and non-biodegradable. Pure carbon is a non-biological solid that is completely biocompatible; that is, there appears to be no recognition of or reaction to pure carbon by living tissue. In addition, carbon is not degraded or changed by a biological environment and, therefore, no degradation products are created to cause reactions. Preparation of a vitreous carbon is now well known in the art and pyrolytic carbon is also commercially available. The vitreous or glassy carbon is non-crystalline but it is also possible to use a crystalline carbon, such as graphite. It will however, be apparent to one skilled in the art, that the implant device can be comprised of other non-porous, biocompatible and non-biodegradable materials such as plastic, ceramic, metal or fabric materials.

Figure 2:
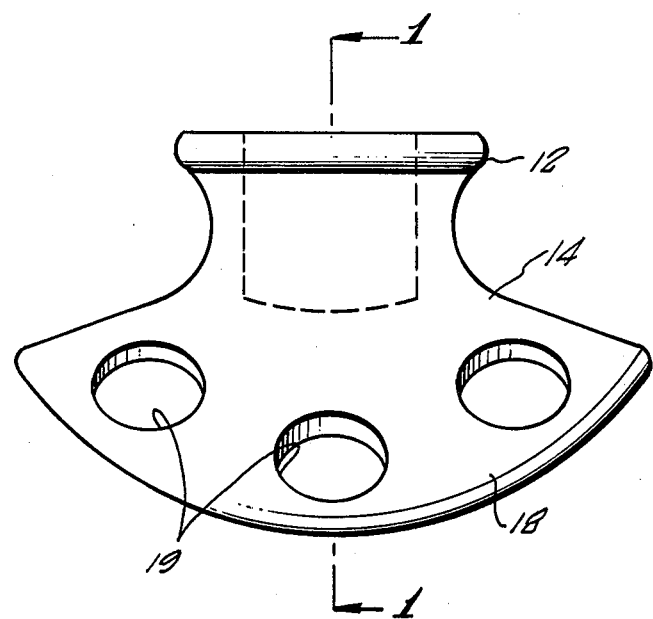
FIG. 2 is a side elevation view of the denture retaining device.

Referring now to FIGS. 1 and 2, there is shown the implant device 10 comprised of barrel portion 12 integrally formed with base portion 14. The barrel portion defines a cavity 15 which preferably has its interior surface 16 serrated or roughened to facilitate recipt and retention of means (not shown) for retaining dentures. The base portion 14 is comprised of a flange 18 which is preferably saddle-shaped. The saddle-shaped flange 18 preferably protrudes outwardly at a suitable angle to fit to the bony ridge, e.g., an angle of about 45° for some locations in the mouth. The flange is preferably provided with a plurality of apertures 19. The apertures function to facilitate permanent attachment of the implant device. As can be seen in FIG. 1, when permanently implanted into the mouth of the patient, the flange 18 of base portion 14 is positioned over the maxillary or mandibulary ridge 20 and mucosa 22 is positioned around the lateral exterior of the device 10.

To implant the retaining device into the mouth of the patient, the mucosa and the subperiosteum are retracted to expose either the maxillary or mandibulary ridge. The size of the ridge is measured and a retaining device having slightly smaller saddle size is selected for implantation. The surface of the bony ridge is then shaved slightly with a bone bur to enable a perfect complementary fit between the saddle of the retaining device and the surface of the ridge. The implant device 10 having a magnet permanently installed therein so that it is flush with the distal surface 24 of barrel 12 is placed over ridge 20. The mucosa 22 is then folded back over the device and sutured. A hole is formed in the mucosa enabling the distal surface 24 of the barrel portion 12 to protrude above the surface of the mucosa 22. During the healing process, fibrous tissue from the mucous membranes grows into the apertures 19 to form a vascularized biological anchor for the device. Furthermore, it is believed that because the bony ridge was traumatized with a bone bur, the bone tissue will also grow into apertures 19 and contiguous to the implant.

After the operation was healed, a magnet having opposite polarity from the magnet installed into the retaining device, is permanently positioned on the surface of the denture by any manner well known in the art. The magnet is positioned on the denture at a location so that when the denture is placed into the mouth of the patient, the two magnets will be contiguous. It is preferred that for each denture, a plurality of retaining devices be permanently implanted into the mouth of the patient. In many cases, three retaining devices will be sufficient. It is preferred that one be positioned at the front of the edentulous ridge and one of the other two be positioned equidistant down each of the respective sides of the ridge, for example, at the site of the first or second molar. In some cases, alternative positioning of the implants will be suitable.

While an embodiment and application of this invention has been shown and described, it will be apparent to those skilled in the art that many more modifications are possible without departing from the inventive concepts herein described. The invention, therefore, is not to be restricted except as is necessary by the prior art and by the spirit of the appended claims.

I claim:

1. An implant device for retaining dentures comprising:

a first portion capable of receiving a denture retaining means, and first portion comprising a barrel having a cavity therein, said first portion being provided with a magnet; and, a base portion integrally formed with said first portion, said base portion having at least one pair of flanges angled with respect to each other such that the device is capable of being implanted over the top of the ridge of the jaw and under the periosteum, said flange being provided with a plurality of apertures, said apertures allowing periosteal tissue ingrowth to permanently secure the device onto the jaw, the exterior surface of said device consisting essentially of a non-porous polymeric carbon.

2. The implant device of claim 1 wherein the outer surface of said device consists essentially of a biocompatible and non-biodegradable material.

3. The implant device of claim 1 wherein the outer surface of said device consists essentially of a polymeric carbon.

4. The implant device of claim 1 wherein said flange is saddle-shaped.

* * * * *